(12) United States Patent
Drysdale et al.

(10) Patent No.: US 8,350,099 B2
(45) Date of Patent: *Jan. 8, 2013

(54) FLUOROVINYL ETHER FUNCTIONALIZED AROMATIC DIESTERS, DERIVATIVES THEREOF, AND PROCESS FOR THE PREPARATION THEREOF

(75) Inventors: Neville Everton Drysdale, Newark, DE (US); Surbhi Mahajan, Newark, DE (US); Kenneth Gene Moloy, Hockessin, DE (US); Fredrik Nederberg, Greenville, DE (US); Joel M. Pollino, Elkton, MD (US); Joachim C. Ritter, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 221 days.

This patent is subject to a terminal disclaimer.

(21) Appl. No.: 12/873,423

(22) Filed: Sep. 1, 2010

(65) Prior Publication Data

US 2011/0218353 A1    Sep. 8, 2011

Related U.S. Application Data

(60) Provisional application No. 61/239,088, filed on Sep. 2, 2009, provisional application No. 61/239,090, filed on Sep. 2, 2009, provisional application No. 61/239,091, filed on Sep. 2, 2009, provisional application No. 61/239,092, filed on Sep. 2, 2009, provisional application No. 61/239,094, filed on Sep. 2, 2009.

(51) Int. Cl.
C07C 17/00    (2006.01)

(52) U.S. Cl. ........ 570/123; 570/101; 570/126; 570/127; 570/163; 570/257; 528/272; 562/405; 562/472; 562/474; 564/134

(58) Field of Classification Search ............... 570/101, 570/122, 123, 124, 125, 126, 127, 129, 130, 570/131, 135, 136, 138, 163, 257; 560/1, 560/8, 55, 60, 62, 63; 562/405, 472, 474; 564/134; 528/272

See application file for complete search history.

(56) References Cited

U.S. PATENT DOCUMENTS

| | | | |
|---|---|---|---|
| 4,219,625 A | 8/1980 | Mares et al. |
| 4,841,093 A | 6/1989 | Tamaru et al. |
| 5,091,456 A | 2/1992 | Rodini |
| 5,104,961 A | 4/1992 | Muller |
| 5,243,019 A | 9/1993 | Takeda et al. |
| 5,349,093 A | 9/1994 | Oka et al. |
| 5,468,882 A | 11/1995 | Schohe-Loop et al. |
| 5,756,814 A | 5/1998 | Lin et al. |
| 6,734,227 B2 | 5/2004 | Jing et al. |
| 6,790,898 B2 | 9/2004 | Lee et al. |
| 6,960,642 B2 | 11/2005 | Jariwala et al. |
| 7,202,324 B2 | 4/2007 | Kim et al. |
| 7,446,127 B2 | 11/2008 | Choi et al. |
| 7,825,280 B2 | 11/2010 | Saegusa et al. |
| 2002/0042526 A1 | 4/2002 | Piscopio et al. |
| 2003/0001130 A1 | 1/2003 | Qiu |
| 2004/0235685 A1 | 11/2004 | Russo et al. |
| 2008/0020148 A1 | 1/2008 | Klein et al. |
| 2008/0039558 A1 | 2/2008 | Lazzari et al. |

FOREIGN PATENT DOCUMENTS

| | | |
|---|---|---|
| EP | 1616849 A2 | 1/2006 |
| JP | 62197419 A | 9/1987 |
| JP | 62205181 A | 9/1987 |
| JP | 1249747 A | 11/1989 |
| JP | 5294903 A | 11/1993 |
| JP | 1017522 A | 1/1998 |
| JP | 2005120001 A | 5/2005 |
| KR | 1020030046554 A | 6/2003 |
| KR | 1020040006591 A | 1/2004 |
| WO | 9967304 A1 | 12/1999 |
| WO | 2006043501 A1 | 4/2006 |

OTHER PUBLICATIONS

Feiring et al, "Synthesis of Arylperfluoroalkyl Ethers by Direct Fluorination", Journal of Fluorine Chemistry, 89 (1998), pp. 31-34.*

Feiring et al, "Novel Aromatic Polymers with Pendant Lithium Perfluoroalkylsulfonate or Sulfonimide Groups", Macromolecules 2000, 33, pp. 9262-9271.*

International Search Report, Related PCT International Application No. PCT/US2010/047472 Mailed May 30, 2011 (Neville Everton Drysdale, Filed Sep. 1, 2010).

International Search Report, Related PCT International Application No. PCT/US2010/047514 Mailed May 18, 2011 (Neville Everton Drysdale et al., Filed Sep. 1, 2010).

International Search Report, Related PCT International Application No. PCT/US2010/047480 Mailed May 18, 2011 (Neville Everton Drysdale et al., Filed Sep. 1, 2010).

Related PCT International Application No. PCT/US2010/049962 (Neville Everton Drysdale, Filed Sep. 23, 2010).

International Search Report, Related PCT International Application No. PCT/US2010/047492 Mailed May 31, 2011 (Neville Everton Drysdale et al., Filed Sep. 1, 2010).

JP2005-120001, Machine Translation, Thomson Innovation (www.thomsoninnovation.com, Sep. 26, 2011).

JP62-197491A, Machine Translation of Abstract Only (www.worldwide.espacenet.com, Sep. 26, 2011).

JP62-205181A, Machine Translation of Abstract Only (www.worldwide.espacenet.com, Sep. 26, 2011).

JP12-49747, Machine Translation of Abstract Only (www.worldwide.espacenet.com, Sep. 26, 2011).

JP52-94903A, Machine Translation of Abstract Only (www.worldwide.espacenet.com, Sep. 26, 2011).

(Continued)

Primary Examiner — Frances Tischler

(57) ABSTRACT

Disclosed are fluorovinyl ether functionalized aromatic diesters and derivatives thereof. The compounds disclosed have utility as functionalized monomers and comonomers in polyesters, polyamides, and the like. It has been found that incorporation of the monomers into polymers provides improved soil resistance to shaped articles produced from the polymers.

24 Claims, No Drawings

OTHER PUBLICATIONS

Co-pending U.S. Appl. No. 12/873,392, Neville Everton Drysdale, filed Sep. 1, 2010.

Co-pending U.S. Appl. No. 12/873,396, Neville Everton Drysdale, filed Sep. 1, 2010.

Co-pending U.S. Appl. No. 12/873,402, Neville Everton Drysdale, filed Sep. 1, 2010.

Co-pending U.S. Appl. No. 12/873,418, Neville Everton Drysdale, filed Sep. 1, 2010.

Co-pending U.S. Appl. No. 12/873,428, Neville Everton Drysdale, filed Sep. 1, 2010.

Feiring, A.E. et al., Aromatic Monomers with Pendant Fluoroalkylsulfonate and Sulfonimide Groups, Journal of Fluorine Chemistry 105(2000), pp. 129-135.

ASTM International, Designation: E29-08, Standard Practice for Using Significant Digits in Test Data to Determine Conformance with Specifications, pp. 1-5.

* cited by examiner

FLUOROVINYL ETHER FUNCTIONALIZED AROMATIC DIESTERS, DERIVATIVES THEREOF, AND PROCESS FOR THE PREPARATION THEREOF

FIELD OF THE INVENTION

The present invention is directed to fluoro-ether functionalized aromatic diesters and derivatives thereof. The compounds disclosed have utility as functionalized monomers and comonomers in polyesters, polyamides, polyoxadiazoles, and the like. It has been found that incorporation of the monomers into polymers provides improved soil resistance, particularly in fibers.

BACKGROUND

Fluorinated materials have many uses. In particular, they are used in the in polymer-related industries, and, more particularly, in fiber-related industries, to impart soil, water and oil resistance, and improved flame retardancy. Generally, these materials are applied as a topical treatment, but their effectiveness decreases over time due to material loss via wear and washing.

There is a need to provide polymeric materials that have improved soil and oil resistance.

SUMMARY OF THE INVENTION

In one aspect, the present invention provides a composition comprising a compound represented by the structure (I)

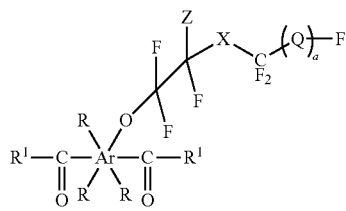

wherein,
Ar represents a benzene or naphthalene radical;
each R is independently H, $C_1$-$C_{10}$ alkyl, $C_5$-$C_{15}$ aryl, $C_6$-$C_{20}$ arylalkyl; OH, or a radical represented by the structure (II)

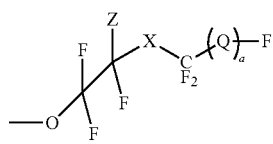

with the proviso that only one R can be OH or the radical represented by the structure (II);
each $R^1$ is independently OH, $C_1$-$C_{10}$ alkoxy, $C_5$-$C_{15}$ aryloxy, $C_6$-$C_{20}$ arylalkoxy; chloro, bromo; or amino;
X is O or $CF_2$;
Z is H, Cl, or Br;
Q represents the structure (Ia)

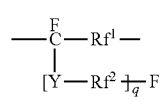

wherein a=0 or 1;
q=0-10;
Y is O or $CF_2$;
$Rf^1$ is $(CF_2)_n$, wherein n is 0-10;
and,
$Rf^2$ is $(CF_2)_p$, wherein p is 0-10, with the proviso that when p is 0, Y is $CF_2$.

In another aspect, the present invention provides a process comprising combining a hydroxy aromatic diester in the presence of a solvent and a catalyst with a compound represented by the structure (III)

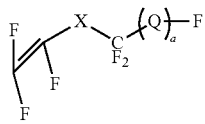

wherein X is O or $CF_2$, and Q represents the structure (Ia)

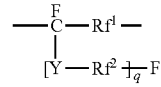

wherein a=0 or 1;
q=0-10;
Y is O or $CF_2$;
$Rf^1$ is $(CF_2)_n$, wherein n is 0-10;
$Rf^2$ is $(CF_2)_p$, wherein p is 0-10, with the proviso that when p is 0, Y is $CF_2$;
to form a first reaction mixture, stirring the first reaction mixture at a temperature within the range from about −70° C. to the reflux temperature of the reaction mixture, and cooling.

DETAILED DESCRIPTION

When a range of numerical values is provided herein, it is intended to encompass the end-points of the range unless specifically stated otherwise. Numerical values used herein have the precision of the number of significant figures provided, following the standard protocol in chemistry for significant figures as outlined in ASTM E29-08 Section 6. For example, the number 40 encompasses a range from 35.0 to 44.9, whereas the number 40.0 encompasses a range from 39.50 to 40.49.

As used herein, the term "fluorovinyl ether aromatic compound" refers to the compound of structure (I). The term "fluorovinyl ether aromatic diester" refers to that subclass of compounds of structure (I) wherein $R^1$ is $C_1$-$C_{10}$ alkoxy, $C_5$-$C_{15}$ aryloxy, or $C_6$-$C_{20}$ arylalkoxy. The term "fluorovinyl ether aromatic diacid" shall refer to that subclass of compounds of structure (I) wherein $R^1$ is —OH. The term "fluorovinyl ether aromatic dihalogenide" refers to that subclass of compounds of structure (I) wherein $R^1$ is —Cl or —Br. The term "fluorovinyl ether aromatic diamine" refers to that subclass of compounds of structure (I) wherein $R^1$ is amine. The term "perfluorovinyl compound" refers to the olefinically unsaturated compound represented by structure (III).

In one aspect, the present invention provides a composition comprising a compound represented by the structure (I)

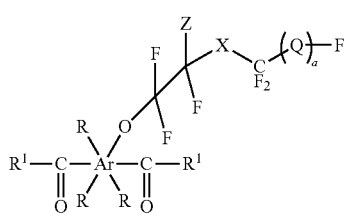

I wherein,
Ar represents a benzene or naphthalene radical;
each R is independently H, $C_1$-$C_{10}$ alkyl, $C_5$-$C_{15}$ aryl, $C_6$-$C_{20}$ arylalkyl; OH, or a radical represented by the structure (II)

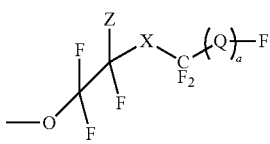

II with the proviso that only one R can be OH or the radical represented by the structure (II);
each $R^1$ is independently OH, $C_1$-$C_{10}$ alkoxy, $C_5$-$C_{15}$ aryloxy, $C_6$-$C_{20}$ arylalkoxy; chloro, bromo; or amino;
X is O or $CF_2$;
Z is H, Cl, or Br;
Q represents structure (Ia)

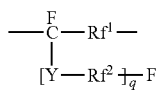

Ia wherein a=0 or 1;
q=0-10;
Y is O or $CF_2$;
$Rf^1$ is $(CF_2)_n$, wherein n is 0-10;
and,
$Rf^2$ is $(CF_2)_p$, wherein p is 0-10, with the proviso that when p is 0, Y is $CF_2$.
In one embodiment, the compound is represented by the structure (IVa)

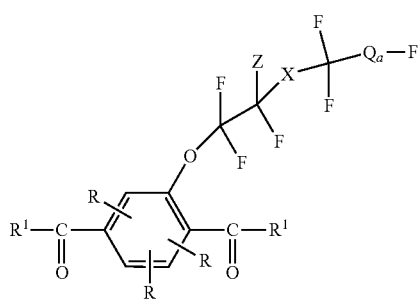

IVa wherein R, $R^1$, Z, X, Q, and a are as recited supra.

In another embodiment, the compound is represented by the structure (IVb).

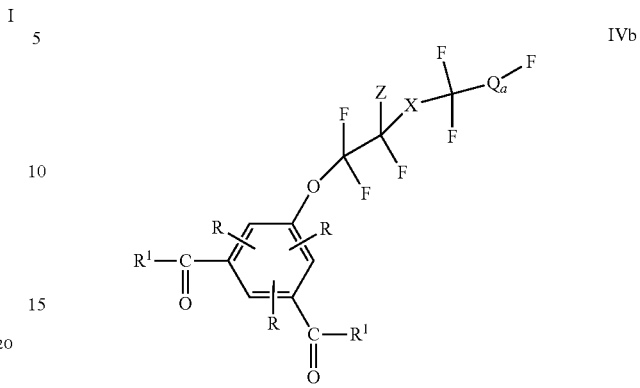

IVb wherein R, $R^1$, Z, X, Q, and a are as recited supra.
As can be noted in the structures above, the substituents can be attached to the aromatic ring at any point, thus making it possible to have ortho-, meta- and para-substituents as defined above.
In one embodiment, one R is OH.
In one embodiment, each R is H.
In one embodiment, one R is OH and the remaining two Rs are each H.
In one embodiment, one R is represented by the structure (II) and the remaining two Rs are each H.
In one embodiment, $R^1$ is C1-C10 alkoxy. In a further embodiment, $R^1$ is methoxy.
In one embodiment, $R^1$ is halogen. In a further embodiment, $R^1$ is chloro.
In one embodiment, $R^1$ is hydroxyl.
In one embodiment, $R^1$ is amino. In a further embodiment, $R^1$ is

In one embodiment, X is O. In an alternative embodiment, X is $CF_2$.
In one embodiment, Y is O. In an alternative embodiment, Y is $CF_2$.
In one embodiment Z is Cl or Br. In a further embodiment, Z is Cl.
In an alternative embodiment, one R is represented by the structure (II), and one Z is H. In a further embodiment, one R is represented by the structure (II), one Z is H, and one Z is Cl.
In one embodiment, $Rf^1$ is $CF_2$.
In one embodiment, $Rf^2$ is $CF_2$.
In one embodiment, $Rf^2$ is a bond (that is, p=0), and Y is $CF_2$.
In one embodiment, each R is H, Z is Cl, $R^1$ is methoxy, X is O, Y is O, $Rf^1$ is $CF_2$, and $Rf^2$ is perfluoropropenyl, and q=1.
In one embodiment, a=0.
In one embodiment, a=1, q=0, and n=0.
In another aspect, the present invention provides a process comprising forming a first reaction mixture by contacting a hydroxy aromatic diester in the presence of a solvent and a catalyst with a perfluoro vinyl compound represented by the structure (III)

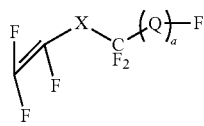

wherein X is O or $CF_2$, and Q represents the structure (Ia)

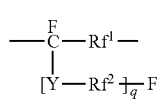

wherein a=0 or 1;
q=0-10;
Y is O or $CF_2$;
$Rf^1$ is $(CF_2)_n$, wherein n is 0-10;
$Rf^2$ is $(CF_2)_p$, wherein p is 0-10, with the proviso that when p is 0, Y is $CF_2$;
at a temperature within the range of about –70° C. to the reflux temperature of the reaction mixture.

In one embodiment, the reaction mixture is agitated during reaction. In one embodiment, the reaction occurs at a temperature above room temperature but below the reflux temperature of the reaction mixture, and the reaction mixture is cooled following reaction. The reaction mixture can be held at the reaction temperature until the desired yield of reaction is achieved.

In one embodiment, the solvent is halogenated, and the process forms a fluorovinyl ether aromatic diester, in which Z is the corresponding halogen. Suitable halogenated solvents include but are not limited to tetrachloromethane, tetrabromomethane, hexachloroethane and hexabromoethane. In an alternative embodiment, the solvent is non-halogenated, and in the resulting fluorovinyl ether aromatic diester, Z is H. Suitable non-halogenated solvents include but are not limited to tetrahydrofuran (THF), dioxane, and dimethylformamide (DMF). Thus, the reactions in the processes herein can be carried out in the presence of a chlorinating reagent that is volatile and can function as both a solvent and a chlorinating agent. Non-halogenated solvents are optional.

The reaction is catalyzed by a base. A variety of basic catalysts can be used, i.e., any catalyst that is capable of deprotonating phenol. That is, a suitable catalyst is any catalyst having a pKa greater than that of phenol (9.95, using water at 25° C. as reference). Suitable catalysts include, but are not limited to, sodium methoxide, calcium hydride, sodium metal, potassium methoxide, and potassium t-butoxide, potassium carbonate and sodium carbonate. Preferred are potassium t-butoxide, potassium carbonate, and sodium carbonate.

The reaction can be terminated at any desirable point by the addition of acid (such as, for example, 10% HCl). Alternatively, when using solid catalysts, such as the carbonate catalysts, the reaction mixture can be filtered to remove the catalyst, thereby terminating the reaction.

Suitable hydroxy aromatic diesters include, but are not limited to, 1,4-dimethyl-2-hydroxy terephthalate, 1,4-diethyl-2-5-dihydroxy terephthalate, 1,3-dimethyl 4-hydroxyisophthalate, 1,3-dimethyl-5-hydroxy isophthalate, 1,3-dimethyl 2-hydroxyisophthalate, 1,3-dimethyl 2,5-dihydroxyisophthalate, 1,3-dimethyl 2,4-dihydroxyisophthalate, dimethyl 3-hydroxyphthalate, dimethyl 4-hydroxyphthalate, dimethyl 3,4-dihydroxyphthalate, dimethyl 4,5-dihydroxyphthalate, dimethyl 3,6-dihydroxyphthalate, dimethyl 4,8-dihydroxynaphthalene-1,5-dicarboxylate, dimethyl 3,7-dihydroxynaphthalene-1,5-dicarboxylate, dimethyl 2,6-dihydroxynaphthalene-1,5-dicarboxylate, or mixtures thereof.

In one embodiment, the hydroxy aromatic diester is 1,4-diethyl-2-5-dihydroxy terephthalate, 1,4-dimethyl-2-hydroxy terephthalate, or 1,3-dimethyl-5-hydroxy isophthalate. In a further embodiment, the hydroxy aromatic diester is 1,4-diethyl-2-5-dihydroxy terephthalate. In an alternative embodiment, the hydroxy aromatic diester is 1,4-dimethyl-2-hydroxy terephthalate. In an alternative embodiment the hydroxy aromatic diester is 1,3-dimethyl-5-hydroxy isophthalate.

Suitable perfluorovinyl compounds include, but are not limited to, 1,1,1,2,2,3,3-heptafluoro-3-(1,1,1,2,3,3-hexafluoro-3-(1,2,2-trifluorovinyloxy)propan-2-yloxy)propane, heptafluoropropyltrifluorovinylether, perfluoropent-1-ene, perfluorohex-1-ene, perfluorohept-1-ene, perfluorooct-1-ene, perfluoronon-1-ene, perfluorodec-1-ene, and mixtures thereof. In one embodiment, the perfluorovinyl compound is 1,1,1,2,2,3,3-heptafluoro-3-(1,1,1,2,3,3-hexafluoro-3-(1,2,2-trifluorovinyloxy)propan-2-yloxy)propane. In an alternative embodiment the perfluorovinyl compound is heptafluoropropyltrifluorovinylether.

In the practice of the process, a suitable hydroxy aromatic diester and a suitable perfluovinyl compound are contacted in the presence of a suitable solvent and a suitable catalyst until the reaction has achieved the desired degree of conversion. In one embodiment, the reaction is continued until no further product is produced over some preselected time scale. The required reaction time to achieve the desired degree of conversion depends upon the reaction temperature, the chemical reactivity of the specific reaction mixture components, and the degree of mixing applied to the reaction mixture, and can be readily determined by one skilled in the art. Progress of the reaction can be monitored using any one of a variety of established analytical methods, including, but not limited to, nuclear magnetic resonance spectroscopy, thin layer chromatography, and gas chromatography. When the desired level of conversion has been achieved, the reaction mixture is quenched, as described supra. In one embodiment, the thus quenched reaction mixture is concentrated under vacuum, and rinsed with a solvent. In one embodiment, a plurality of compounds encompassed by the structure (I) can be made in a single reaction mixture. In such cases, separation of the products thus produced can be effected by any method known to the skilled artisan such as, for example, distillation or column chromatography.

In one embodiment the process further comprises contacting the fluorovinyl ether aromatic diester produced supra with an aqueous base, preferably a strong base such as KOH or NaOH, in aqueous solution to form a reaction mixture, heating the reaction mixture to reflux, then cooling the mixture to room temperature, followed by acidifying the mixture, preferably with a strong acid, such as HCl or $H_2SO_4$, until the pH is 0 to 2, preferably pH is 1. The reaction mixture can be held at reflux temperature until the desired progress of reaction is achieved. The acidification thus performed causes the precipitation of the fluorovinyl ether aromatic diacid thereby produced. The thus precipitated diacid can then be isolated via filtration and recrystallization from appropriate solvents (e.g., ethyl acetate). The progress of the reaction can be followed by any convenient method, including but not limited to thin layer chromatography, gas chromatography and NMR.

In a further embodiment, the process further comprises contacting the so prepared fluorovinyl ether aromatic diacid with a chloride selected from SOCl$_2$, PCl$_3$, PCl$_5$, and oxalylchloride to form the associated perfluorovinyl ether aromatic diacid chloride. In one embodiment, the chloride is SOCl$_2$.

In an alternative embodiment, the process further comprises contacting the fluorovinyl ether aromatic diester with an amine to form a second reaction mixture, heating the reaction mixture to reflux, cooling and then adding the reaction mixture to water to precipitate out the thus produced fluorovinyl ether aromatic diamine. The reaction mixture can be held at reflux temperature until the desired progress of reaction is achieved. The progress of the reaction can be followed by any convenient method, including but not limited to thin layer chromatography, gas chromatography and nmr. The fluorovinyl ether aromatic diamine can be purified by recrystallization or by column chromatography or other methods known to those skilled in the art. In one embodiment, the amine is hydrazine.

Once the fluorovinyl ether aromatic compound has been prepared, it is suitable for polymerization, among other potential uses such as intermediates for surface protection compositions, pharmaceutical and agricultural chemicals.

The invention is further described and illustrated in but not limited to the following specific embodiments.

EXAMPLES

The chemicals and reagents were used as received in the Examples as follows:

From Sigma-Aldrich, Milwaukee, Wis.:
potassium t-butoxide
tetrahydrofuran (THF)
dimethyl formamide (DMF)
dichloromethane
trichloromethane (chloroform)
tetrachloromethane (carbon tetrachloride)
tetrabromomethane (carbon tetrabromide)
hydrochloric acid (HCl)
hexane
acetic acid
anhydrous sodium sulfate
dimethyl 5-hydroxyisophthalate
diethyl 2,5-dihydroxy terephthalate
1,4-dimethyl-2-hydroxy terephthalate
1,3-dimethyl-5-hydroxy isophthalate
1,4-dimethyl-2,5-dihydroxy terephthalate
potassium hydroxide (KOH)
ethyl acetate (EtOAc)
thionyl chloride
hydrazine monohydrate From SynQuest Labs., Alachua, Fla.:
1,1,1,2,2,3,3-heptafluoro-3-(1,1,1,2,3,3-hexafluoro-3-(1,2,2-trifluorovinyloxy)propan-2-yloxy)propane
heptafluoropropyltrifluorovinylether

Example 1

Preparation of: (Diethyl 2,5-bis(2-chloro-1,1,2-trifluoro-2-(perfluoropropoxy)ethoxy)terephthalate (A); (Diethyl 2-(2-chloro-1,1,2-trifluoro-2-(perfluoropropoxy)ethoxy)-5-(1,1,2-trifluoro-2-(perfluoropropoxy)ethoxy)terephthalate (B); diethyl 2-(2-chloro-1,1,2-trifluoro-2-(perfluoropropoxy)ethoxy)-5-hydroxyterephthalate (C)

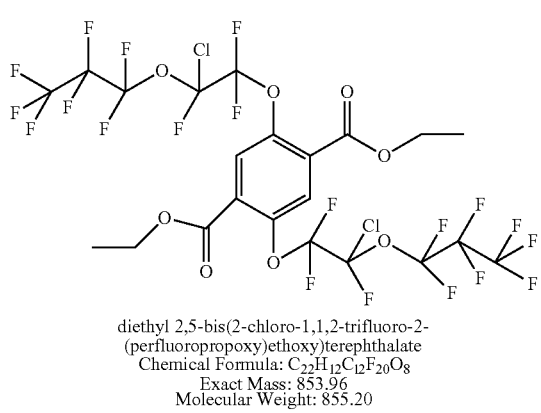

A diethyl 2,5-bis(2-chloro-1,1,2-trifluoro-2-(perfluoropropoxy)ethoxy)terephthalate
Chemical Formula: C$_{22}$H$_{12}$Cl$_2$F$_{20}$O$_8$
Exact Mass: 853.96
Molecular Weight: 855.20

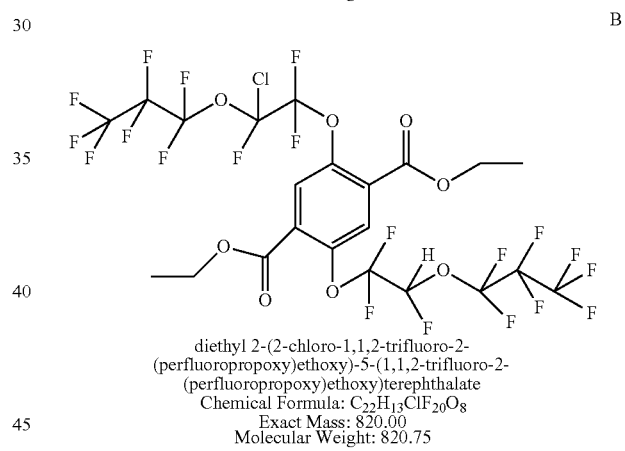

B diethyl 2-(2-chloro-1,1,2-trifluoro-2-(perfluoropropoxy)ethoxy)-5-(1,1,2-trifluoro-2-(perfluoropropoxy)ethoxy)terephthalate
Chemical Formula: C$_{22}$H$_{13}$ClF$_{20}$O$_8$
Exact Mass: 820.00
Molecular Weight: 820.75

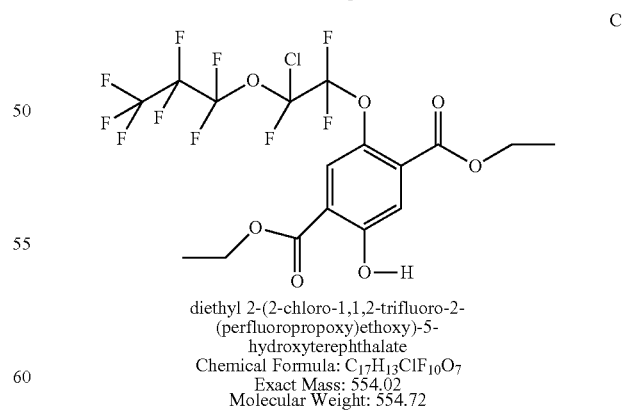

C diethyl 2-(2-chloro-1,1,2-trifluoro-2-(perfluoropropoxy)ethoxy)-5-hydroxyterephthalate
Chemical Formula: C$_{17}$H$_{13}$ClF$_{10}$O$_7$
Exact Mass: 554.02
Molecular Weight: 554.72

Heptafluoropropyltrifluorovinylether (2.66 g, 0.01 mol) was charged into a reaction flask containing diethyl 2,5-dihydroxy terephthalate (1.27 g, 0.005 mol), potassium t-butoxide (1.12 g, 0.01 mol), dimethyl formamide (10 mL), and tetrachloromethane (50 mL) to form a reaction mixture. After stirring for 24 hours at room temperature, the reaction mixture was poured into a water-ice mixture (~200 mL) containing acetic acid (~2 mL). This resulting mixture was washed with dichloromethane (3×100 mL), then dried over anhydrous sodium sulfate. The sodium sulfate was filtered out of the mixture and the separated filtrate was concentrated at reduced pressure and then purified by column chromatography to give the di-substituted material, compound A (diethyl 2,5-bis(2-chloro-1,1,2-trifluoro-2-(perfluoropropoxy)ethoxy)terephthalate, structure shown above), as a white solid, 1.95 g, (45.61% yield) g, $R_f$ 0.90 (1:1 dichloromethane/hexane). Compound B (diethyl 2-(2-chloro-1,1,2-trifluoro-2-(perfluoropropoxy)ethoxy)-5-(1,1,2-trifluoro-2-(perfluoropropoxy)ethoxy)terephthalate, structure shown above) was obtained in a 0.22 g quantity (5.36% yield) and compound C (diethyl 2-(2-chloro-1,1,2-trifluoro-2-(perfluoropropoxy)ethoxy)-5-hydroxyterephthalate, structure shown above) was obtained in 0.66 g quantity (22.74% yield).

Example 2

Preparation of Diethyl 2,5-bis(2-chloro-1,1,2-trifluoro-2-(perfluoropropoxy)ethoxy)terephthalate (A); (Diethyl 2-(2-chloro-1,1,2-trifluoro-2-(perfluoropropoxy)ethoxy)-5-(1,1,2-trifluoro-2-perfluoropropoxy)ethoxy)terephthalate (B)

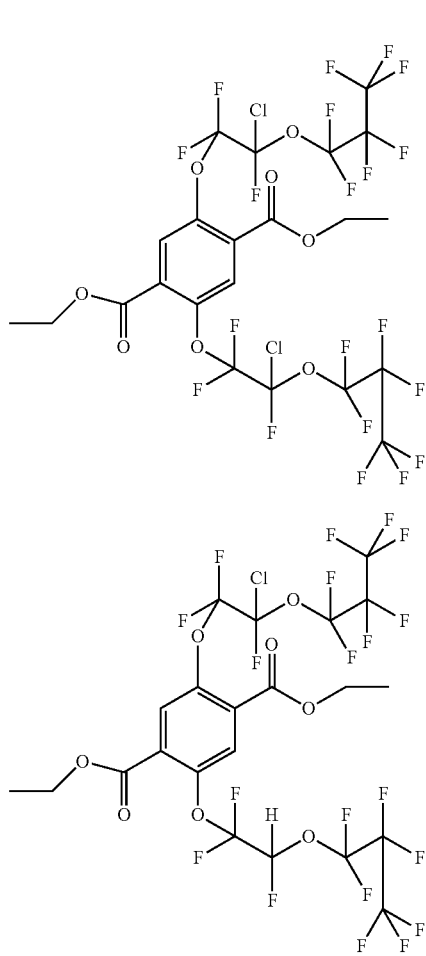

Heptafluoropropyltrifluorovinylether (2.66 g, 0.01 mol) was charged into a reaction flask containing diethyl 2,5-dihydroxy terephthalate (1.27 g, 0.005 mol), potassium t-butoxide (1.12 g, 0.01 mol), dimethyl formamide (10 mL) and tetrachloromethane (50 mL) to form a reaction mixture. After stirring the reaction mixture for 24 hours at room temperature, the reaction mixture was poured into a water-ice mixture (~200 mL) containing acetic acid (~2 mL). This resulting mixture was washed with dichloromethane (3×100 mL), then dried over anhydrous sodium sulfate. The sodium sulfate was separated from the resulting mixture by filtration. The separated filtrate was concentrated at reduced pressure and then purified by column chromatography to give the di-substituted material, compound A (diethyl 2,5-bis(2-chloro-1,1,2-trifluoro-2-(perfluoropropoxy)ethoxy)terephthalate), as a white solid, 1.62 g, $R_f$ 0.90 (1:1 dichloromethane/hexane) of melting point 65° C. (as shown by differential scanning calorimetry, DSC). Compound B (diethyl 2-(2-chloro-1,1,2-trifluoro-2-(perfluoropropoxy)ethoxy)-5-(1,1,2-trifluoro-2-perfluoropropoxy)ethoxy)terephthalate) was obtained only in a few milligram quantity, $R_f$ 0.80 (1:1 dichloromethane/hexane).

Example 3

Preparation of: (Dimethyl 2-(2-chloro-1,1,2-trifluoro-2-(1,1,2,3,3,3-hexafluoro-2-perfluoropropoxy)propoxy)ethoxy)terephthalate

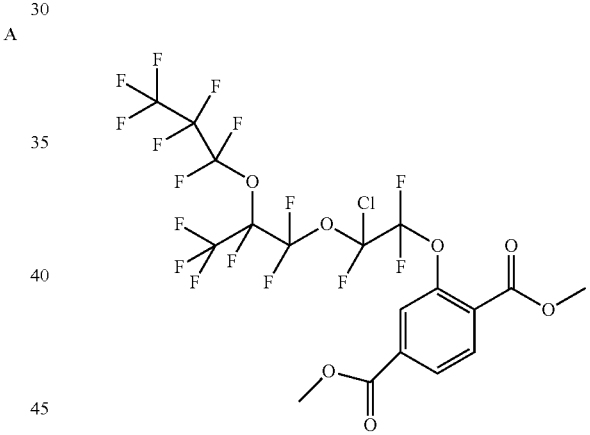

In a dry box, 1,4-dimethyl-2-hydroxy terephthalate (1.05 g, 0.005 mol) was added to an oven-dried 100 mL reaction flask equipped with a stirring bar and a pressure equaling (PE) addition funnel. Dimethyl formamide (DMF, 10.0 mL) and tetrachloromethane (50 mL) were then added to the reaction flask and the reaction mixture was then stirred until a homogeneous solution resulted. Potassium t-butoxide (0.154 g, 0.001375 mol) was added to the reaction flask, resulting in a heterogeneous mixture.

Via the PE funnel, 1,1,1,2,2,3,3-heptafluoro-3-(1,1,1,2,3,3-hexafluoro-3-(1,2,2trifluorovinyloxy)propan-2-yloxy)propane (5.40 g, 0.0125 mol) was added to the reaction mixture. The reaction mixture was allowed to stir at room temperature (about 25° C.) for ~24 hours. The reaction was quenched by the addition for 2 mL of 10% HCl. The resulting reaction material was concentrated at reduced pressure. This material was then dissolved in dichloromethane (~150 mL) and then washed with 10% HCl (2×25 mL) and then with water (~25 mL) to form an organic phase and an aqueous phase. The separated organic phase was then dried over anhydrous sodium sulfate. The sodium sulfate was then filtered off and the filtrate concentrated at reduced pressure to produce a crude material. NMR of this crude material showed only the desired material, dimethyl 2-(2-chloro-1,1,2-trifluoro-2-(1,1,2,3,3,3-hexafluoro-2-perfluoropropoxy)propoxy)ethoxy) terephthalate, and a small amount of dimethyl formamide, present. This crude material was then purified by column chromatography ($R_f$ 0.50 dichloromethane (1)/Hexane (1)) to give the pure material, dimethyl 2-(2-chloro-1,1,2-trifluoro-2-(1,1,2,3,3,3-hexafluoro-2-perfluoropropoxy)propoxy) ethoxy)terephthalate, as a clear oil, 2.60 g (76.92% yield).

Example 4

Preparation of Dimethyl 2-(2-bromo-1,1,2-trifluoro-2-(perfluoropropoxy)ethoxy)terephthalate

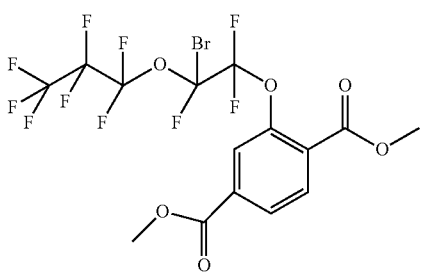 [SMILES: COC(=O)c1ccc(C(=O)OC)c(OC(F)(F)C(F)(Br)OC(F)(F)C(F)(F)C(F)(F)F)c1]

In a dry box, 1,4-dimethyl-2-hydroxy terephthalate (1.05 g, 0.005 mol) was added to an oven-dried 100 mL reaction flask equipped with a stirring bar and a pressure equaling (PE) addition funnel. Dimethyl formamide (20.0 mL) and carbon tetrabromide (12.5 g) were then added to the reaction flask, and the reaction mixture was stirred until a homogeneous solution resulted. Potassium t-butoxide (0.154 g, 0.001375 mol) was added to the reaction flask, resulting in a heterogeneous mixture. Via the PE funnel, heptafluoropropyltrifluorovinylether (3.325 g, 0.0125 mol) was added. The reaction mixture was allowed to stir at room temperature (about 25° C.) for ~24 hours. The reaction was quenched by the addition for 2 mL of 10% HCl. The resulting material in the reaction flask was concentrated at reduced pressure. This material was then dissolved in dichloromethane (~150 mL) and then washed with 10% HCl (2×25 mL) and then with water (~25 mL) to form an organic phase and an aqueous phase. The separated organic phase was then dried over anhydrous sodium sulfate. The sodium sulfate was then filtered off and the filtrate concentrated at reduced pressure to form a crude material. NMR of this crude material only showed the desired material, dimethyl 2-(2-bromo-1,1,2-trifluoro-2-(perfluoropropoxy)ethoxy)terephthalate, and small amounts of dimethyl formamide and carbon tetrabromide present. This crude material was then purified by column chromatography to give the pure material, dimethyl 2-(2-bromo-1,1,2-trifluoro-2-(perfluoropropoxy)ethoxy)terephthalate, as a clear oil, 2.280 g (82.31% yield).

Example 5

Preparation of Dimethyl 2-(2-bromo-1,1,2,3,3,4,4,5,5,6,6,7,7,8,8,8-hexadecafluorooctyloxy)terephthalate

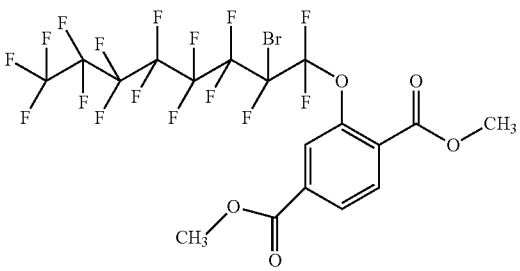 [SMILES: COC(=O)c1ccc(C(=O)OC)c(OC(F)(F)C(F)(Br)C(F)(F)C(F)(F)C(F)(F)C(F)(F)C(F)(F)C(F)(F)F)c1]

In a dry box, 1,4-dimethyl-2-hydroxy terephthalate (1.05 g, 0.005 mol) was added to an oven-dried 100 mL reaction flask equipped with a stirring bar and a pressure equaling (PE) addition funnel. Dimethyl formamide (DMF, 20.0 mL) and carbon tetrabromide (12.5 g) were then added to the reaction flask and the reaction mixture was stirred until a homogeneous solution resulted. Potassium t-butoxide (0.154 g, 0.001375 mol) was added to the reaction flask, resulting in a heterogeneous mixture. Via the PE funnel, (3.325 g, 0.0125 mol) was added to the reaction flask. The reaction mixture was allowed to stir at room temperature (about 25° C.) for ~24 hours. The reaction was quenched by the addition for 2 mL of 10% HCl. The resulting material in the reaction flask was concentrated at reduced pressure. This material was then dissolved in dichloromethane (~150 mL) and then washed with 10% HCl (2×25 mL) and then with water (~25 mL) to form an organic phase and an aqueous phase. The separated organic phase was then dried over anhydrous sodium sulfate. The sodium sulfate was then filtered off and the filtrate concentrated at reduced pressure to form a crude material. This crude material was then purified by column chromatography to give the pure material, dimethyl 2-(2-bromo-1,1,2,3,3,4,4,5,5,6,6,7,7,8,8,8-hexadecafluorooctyloxy)terephthalate, as an oil, 2.22 g (64.5% yield).

Example 6

Preparation of Dimethyl 2-(2-chloro-1,1,2-trifluoro-2-(perfluoropropoxy)ethoxy)terephthalate

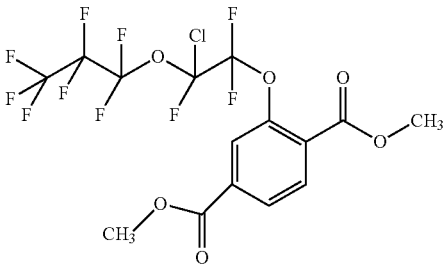 [SMILES: COC(=O)c1ccc(C(=O)OC)c(OC(F)(F)C(F)(Cl)OC(F)(F)C(F)(F)C(F)(F)F)c1]

In a dry box, 1,4-dimethyl-2-hydroxy terephthalate (35.85 g, 0.185 mol) was added to an oven-dried round bottom reaction flask equipped with a stirring bar and a pressure equaling (PE) addition funnel. Dimethyl formamide (DMF, 170.70.0 mL) and tetrachloromethane (~853 mL) were then added to the reaction flask and the reaction mixture was stirred until a homogeneous solution resulted. Potassium t-butoxide (0.154 g, 0.001375 mol) was added to the reaction flask, resulting in a heterogeneous mixture. Via the PE funnel, heptafluoropropyltrifluorovinylether (113.51 g, 0.426 mol) was added. The resulting reaction mixture was allowed to stir at room temperature (about 25° C.) for ~24 hours. The reaction was quenched by the addition for 50 mL of 10% HCl. The resulting material in the reaction flask was concentrated at reduced pressure. This material was then dissolved in dichloromethane and then washed with 10% HCl (2x) and then with water to form an organic phase and an aqueous phase. The separated organic phase was then dried over anhydrous sodium sulfate. The sodium sulfate was then filtered off and the filtrate concentrated at reduced pressure to form a crude material. This crude material was then purified by column chromatography to give the pure material, dimethyl 2-(2-chloro-1,1,2-trifluoro-2-(perfluoropropoxy)ethoxy)terephthalate, as an oil, 80.56 g (92.49% yield).

Example 7

Preparation of Dimethyl 5-(2-bromo-1,1,2-trifluoro-2-(1,1,2,3,3,3-hexafluoro-2-(perfluoropropoxy)propoxy)ethoxy)isophthalate

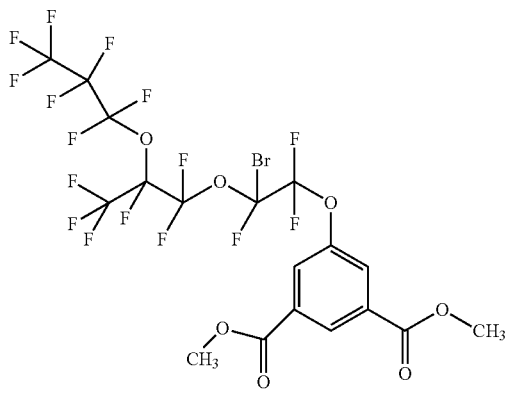 [SMILES: COC(=O)c1cc(OC(F)(F)C(F)(Br)OC(F)(F)C(F)(OC(F)(F)C(F)(F)C(F)(F)F)C(F)(F)F)cc(C(=O)OC)c1]

In a dry box, 1,3-dimethyl-5-hydroxy isophthalate (42.00 g, 0.20 mol) was added to an oven-dried multiple neck reaction flask equipped with a stirring bar and a pressure equaling (PE) addition funnel. Dimethyl formamide (DMF, 500 mL) and carbon tetrabromide (200 g) were then added to the reaction flask to form a reaction mixture and stirred until a homogeneous solution resulted. Potassium t-butoxide (6.16 g, 0.055 mol) was added to the reaction flask, resulting in a heterogeneous mixture. Via the PE funnel, 1,1,1,2,2,3,3-heptafluoro-3-(1,1,1,2,3,3-hexafluoro-3-(1,2,2trifluorovinyloxy)propan-2-yloxy)propane (216.0 g, 0.50 mol) was added to the reaction flask. The resulting reaction mixture was allowed to stir at room temperature (about 25° C.) for ~24 hours. The reaction was quenched by the addition for 80 mL of 10% HCl, resulting in two phases, organic and aqueous. The bottom aqueous phase was removed and washed with 10% HCl (2x250 mL). The separated organic phase was filtered through a silica gel (100 g) and washed with dichloromethane. The resulting material was concentrated at reduced pressure and then purified by column chromatography. The resulting material was then fractionally vacuum distilled affording the 92.84 g (64.38%) of product, dimethyl 5-(2-bromo-1,1,2-trifluoro-2-(1,1,2,3,3,3-hexafluoro-2-(perfluoropropoxy)propoxy)ethoxy)isophthalate, boiling at 140-145° C. at 0.46 torr.

Example 8

Preparation of dimethyl 5-(2-chloro-1,1,2-trifluoro-2-(1,1,2,3,3,3-hexafluoro-2-(perfluoropropoxy)propoxy)ethoxy)isophthalate

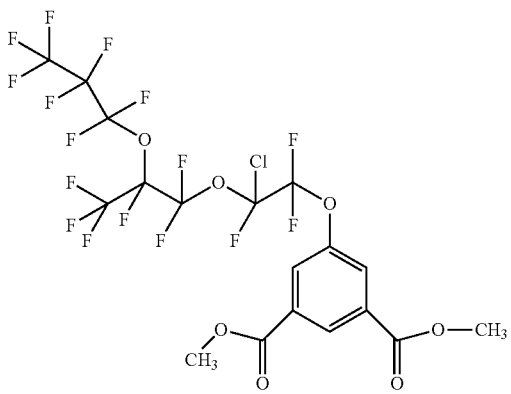 [SMILES: COC(=O)c1cc(OC(F)(F)C(F)(Cl)OC(F)(F)C(F)(OC(F)(F)C(F)(F)C(F)(F)F)C(F)(F)F)cc(C(=O)OC)c1]

In a dry box, 1,3-dimethyl-5-hydroxy isophthalate (42.00 g, 0.20 mol) was added to an oven-dried multiple neck reaction flask equipped with a stirring bar and a pressure equaling (PE) addition funnel. Dimethyl formamide (DMF, 200 mL) and tetrachloromethane (1000 mL) were then added to the reaction flask, and stirred until a homogeneous solution resulted. Potassium t-butoxide (6.16 g, 0.055 mol) was added to the reaction flask, resulting in a heterogeneous mixture. Via the PE funnel, 1,1,1,2,2,3,3-heptafluoro-3-(1,1,1,2,3,3-hexafluoro-3-(1,2,2trifluorovinyloxy)propan-2-yloxy)propane (216 g, 0.50 mol) was then added to the reaction flask. The reaction mixture was allowed to stir at room temperature (about 25° C.) for ~24 hours. The reaction was quenched by the addition for 80 mL of 10% HCl. The resulting material in the reaction flask was concentrated at reduced pressure. This material was then dissolved in dichloromethane and then washed with 10% HCl (2x250 mL) and then with water (3x100 mL) to form an organic phase and an aqueous phase. The separated organic phase was then dried over anhydrous sodium sulfate. The sodium sulfate was then filtered off and the filtrate concentrated at reduced pressure and then purified by column chromatography to give 93.4 g (69.08%) yield of the desired material, dimethyl 5-(2-chloro-1,1,2-trifluoro-2-(1,1,2,3,3,3-hexafluoro-2-(perfluoropropoxy)propoxy) ethoxy)isophthalate.

Example 9

Preparation of Dimethyl 5-(2-chloro-1,1,2-trifluoro-2-(perfluoropropoxy)ethoxy)isophthalate

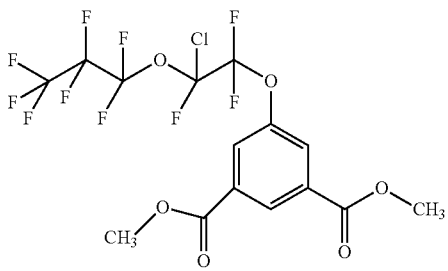 [SMILES: COC(=O)c1cc(OC(F)(F)C(F)(Cl)OC(F)(F)C(F)(F)C(F)(F)F)cc(C(=O)OC)c1]

In a dry box, 1,3-dimethyl-5-hydroxy isophthalate (42.00 g, 0.20 mol) was added to an oven-dried multiple neck reaction flask equipped with a stirring bar and a pressure equaling (PE) addition funnel. Dimethyl formamide (DMF, 200 mL) and tetrachloromethane (1000 mL) were then added to the reaction flask and the resulting reaction mixture was stirred until a homogeneous solution resulted. Potassium t-butoxide (6.16 g, 0.055 mol) was added to the reaction flask, resulting in a heterogeneous mixture. Via the PE funnel, heptafluoropropyltrifluorovinylether (133.0 g, 0.506 mol) was added to the reaction flask. The reaction mixture was allowed to stir at room temperature (about 25° C.) for ~24 hours. The reaction was quenched by the addition for 80 mL of 10% HCl. The resulting material in the reaction flask was concentrated at reduced pressure. This material was then dissolved in dichloromethane and then washed with 10% HCl (2×100) and then with water (1×100 mL) to form an organic phase and an aqueous phase. The separated organic phase was then dried over anhydrous sodium sulfate. The sodium sulfate was then filtered off and the filtrate was concentrated at reduced pressure to form a crude material. This crude material was then purified by column chromatography to give the pure material, dimethyl 5-(2-chloro-1,1,2-trifluoro-2-(perfluoropropoxy) ethoxy)isophthalate, as an oil, 87.54 g (85.72% yield).

Example 10

(Dimethyl 2-(1,1,2-trifluoro-2-(1,1,2,3,3,3-hexafluoro-2-(perfluoropropoxy)propoxy)ethoxy) terephthalate

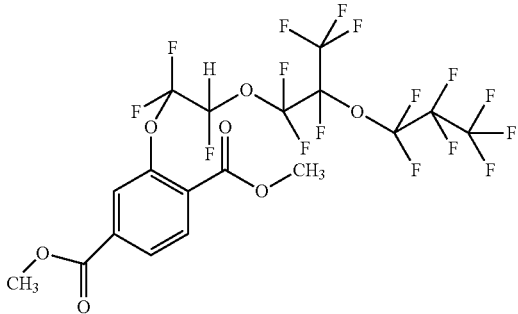 [SMILES: COC(=O)c1ccc(C(=O)OC)c(OC(F)(F)C(F)OC(F)(F)C(F)(OC(F)(F)C(F)(F)C(F)(F)F)C(F)(F)F)c1]

In a dry box, 1,4-dimethyl-2-hydroxy terephtalate (30.25 g, 0.144 mol) was added to an oven-dried multiple neck 500 mL reaction flask equipped with a stirring bar and a pressure equaling (PE) addition funnel. Tetrahydrofuran (THF, 288 mL) was then added to the 1,4-dimethyl-2-hydroxy terephthalate in the reaction flask, and the mixture was stirred until a homogeneous solution resulted. Potassium t-butoxide (4.435 g, 0.040 mol) was added to the reaction flask, resulting in a heterogeneous mixture. Via the PE funnel, 1,1,1,2,2,3,3-heptafluoro-3-(1,1,1,2,3,3-hexafluoro-3-(1,2,2trifluorovinyloxy)propan-2-yloxy)propane (155.52 g, 0.36 mol) was added to the reaction flask. The reaction mixture was allowed to stir at room temperature for ~40 hours. The reaction was then quenched by the addition of 5 mL of 10% HCl. The resulting material in the reaction flask was concentrated at reduced pressure. This material was then dissolved in dichloromethane (~300 mL) and then washed with 10% HCl (2×75 mL) and then with water (~75 mL) to form an organic phase and an aqueous phase, which were then separated. The separated organic phase was then dried over anhydrous sodium sulfate. The sodium sulfate was then filtered off and the remaining material concentrated at reduced pressure and then fractionally vacuum distilled. The fractions boiling within the range of 134-136° C. at 1.4-1.1 torr (84.55 g, 91.4 yield) and 136-138 at 1.1 torr (3.35 g) (combined yield: 95.04%) were collected. NMRs of these samples were shown to be the desired material, dimethyl 2-(1,1,2-trifluoro-2-(1,1,2,3,3,3-hexafluoro-2-(perfluoropropoxy)propoxy)ethoxy)terephthalate.

Example 11

(Diethyl 2,5-bis(1,1,2-trifluoro-2-(perfluoropropoxy) ethoxy)terephthalate (di-substituted) and Diethyl 2-hydroxy-5-(1,1,2-trifluoro-2-(1,1,2,3,3,3-hexafluoro-2-(perfluoropropoxy)propoxy)ethoxy) terephthalate (mono-substituted)

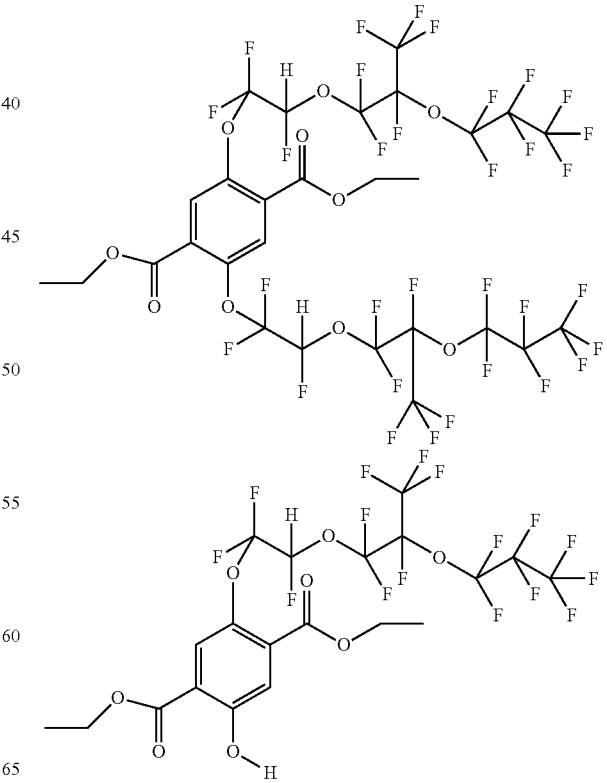

In a dry box, 1,4-diethyl-2,5-dihydroxy terephthalate (1.27 g, 0.005 mol) was added to an oven-dried multiple neck 250 mL reaction flask equipped with a stirring bar and a pressure equaling (PE) addition funnel. Tetrahydrofuran (THF, 100 mL) was then added to the 1,4-diethyl-2,5-dihydroxy terephthalate in the reaction flask and the mixture was stirred until a homogeneous solution resulted. Potassium t-butoxide (0.224 g, 0.002 mol) was added to the reaction flask, resulting in a heterogeneous mixture. Via the PE funnel, 1,1,1,2,2,3,3-heptafluoro-3-(1,1,1,2,3,3-hexafluoro-3-(1,2,2-trifluorovinyloxy)propan-2-yloxy)propane (8.64 g, 0.02 mol) was added to the reaction flask. The reaction mixture was allowed to stir at room temperature for ~2 hours. The reaction was then quenched by the addition for 2 mL of 10% HCl. The resulting material in the reaction flask was concentrated at reduced pressure. This material was then dissolved in dichloromethane (~300 mL) and then washed with 10% HCl (2×50 mL) and then with water (~50 mL) to form an organic phase and an aqueous phase, which were then separated. The separated organic phase was then dried over anhydrous sodium sulfate. The sodium sulfate was then filtered off and the remaining material concentrated at reduced pressure. The crude product was purified by column chromatography to give the resulting diethyl 2,5-bis(1,1,2-trifluoro-2-(perfluoropropoxy)ethoxy)terephthalate (di-substituted, 2.10 g) and diethyl 2-hydroxy-5-(1,1,2-trifluoro-2-(1,1,2,3,3,3-hexafluoro-2-(perfluoropropoxy)propoxy)ethoxy)terephthalate (mono-substituted, 0.22 g) products.

Example 12

(Diethyl 2,5-bis(1,1,2-trifluoro-2-(perfluoropropoxy)ethoxy)terephthalate and Diethyl 2-hydroxy-5-(1,1,2-trifluoro-2-(perfluoropropoxy)ethoxy)terephthalate)

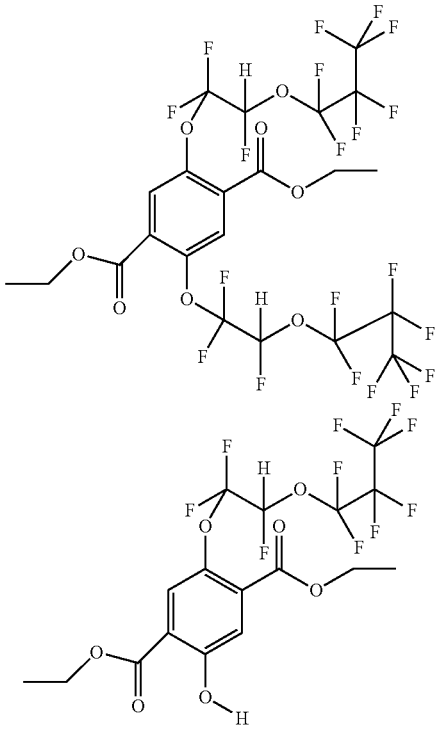

Heptafluoropropyltrifluorovinylether (1.463 g, 0.0055 mol) was charged to a reaction flask containing diethyl 2,5-dihydroxy terephthalate (1.27 g, 0.005 mol), potassium t-butoxide (0.616 g, 0.0055 mol) and dimethyl formamide (DMF, 50 mL) to form a reaction mixture. After stirring for 24 hours at room temperature, the reaction mixture was poured into a water-ice mixture (~200 mL) containing acetic acid (~2 mL). This resulting mixture was then washed with dichloromethane (3×100 mL), then combined with, and dried over, anhydrous sodium sulfate. The mixture was filtered to remove the sodium sulfate, and the separated filtrate was then concentrated at reduced pressure. NMR analysis showed the material to contain a large amount of DMF. Thus, the material was then diluted with dichloromethane and washed with 2% acetic acid solution, thus forming an organic phase and an aqueous phase. The resulting organic phase was dried over anhydrous sodium sulfate, separated from the sodium sulfate by filtration, and concentrated at reduced pressure to form a crude product. The crude product was purified by column chromatography to give the products diethyl 2,5-bis(1,1,2-trifluoro-2-(perfluoropropoxy)ethoxy)terephthalate and diethyl 2-hydroxy-5-(1,1,2-trifluoro-2-(perfluoropropoxy)ethoxy)terephthalate). The di-substituted material was obtained at an $R_f$ value of 0.45 and the mono-substituted material was obtained at $R_f$ of 0.25 (solvent: 1:1 dichloromethane/hexane).

Example 13

(Dimethyl 2-(1,1,2-trifluoro-2-perfluoropropoxy)ethoxy)terephthalate

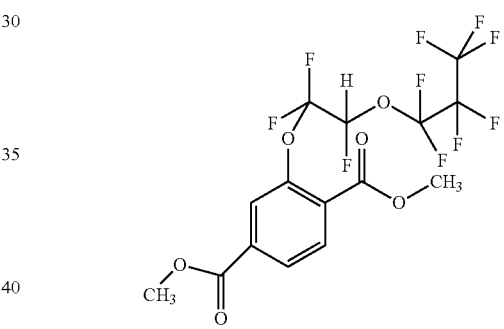

In a dry box, 1,4-dimethyl-2-hydroxy terephthalate (1.05 g, 0.005 mol) was added to an oven-dried multiple neck 100 mL reaction flask equipped with a stirring bar and a pressure equaling (PE) addition funnel. Tetrahydrofuran (THF, 50 mL) was then added and the resulting reaction mixture was stirred until a homogeneous solution resulted. Potassium t-butoxide (0.154 g, 0.0014 mol) was added to the reaction mixture, resulting in a heterogeneous mixture. Via the PE funnel, heptafluoropropyltrifluorovinylether (3.00 g, 0.0125 mol) was added to the reaction flask. The reaction was allowed to stir at room temperature for ~24 hours. The reaction was then quenched by the addition for 2 mL of 10% HCl. The resulting material in the reaction flask was concentrated at reduced pressure. This material was then dissolved in dichloromethane (~150 mL) and then washed with 10% HCl (2×75 mL) and then with water (~75 mL) to form an organic phase and an aqueous phase. The separated organic phase was then dried over anhydrous sodium sulfate. The sodium sulfate was then filtered off and the resulting material concentrated at reduced pressure resulting in 2.09 g of crude material. NMR analyses of this showed it was mostly dimethyl 2-(1,1,2-trifluoro-2-perfluoropropoxy)ethoxy)terephthalate.

Vacuum distillation of this material resulted in producing 1.40 g of purified dimethyl 2-(1,1,2-trifluoro-2-perfluoropropoxy)ethoxy)terephthalate, which boiled at 95-97° C. at 0.3 torr.

Example 14

(Dimethyl 5-(1,1,2-trifluoro-2-(perfluoropropoxy)ethoxy)isophthalate)

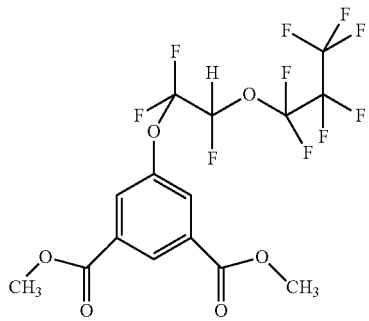 [SMILES: COC(=O)c1cc(OC(F)(F)C(F)OC(F)(F)C(F)(F)C(F)(F)F)cc(C(=O)OC)c1]

In a dry box, dimethyl 5-hydroxyisophthalate (63.0 g, 0.300 mol) was added to an oven-dried multiple neck reaction flask equipped with a stirring bar and a pressure equaling (PE) addition funnel. Tetrahydrofuran (THF, 1500 mL) was then added to the reaction flask, and the reaction mixture was stirred until a homogeneous solution resulted. Potassium t-butoxide (9.24 g, 0.0825 mol) was added to the reaction mixture, resulting in a heterogeneous mixture. Via the PE funnel, heptafluoropropyltrifluorovinylether (199.2 g, 0.075 mol) was added to the reaction flask to form a reaction mixture. The reaction mixture was allowed to stir at room temperature for ~24 hours. The reaction was quenched by the addition for 80 mL of 10% HCl to the reaction flask to form a reaction material. The resulting material was concentrated at reduced pressure. The material was then dissolved in dichloromethane (~150 mL) and then washed with 10% HCl (2×100 mL) and then with water (~100 mL) to form an organic phase and an aqueous phase. The separated organic phase was then dried over anhydrous sodium sulfate. The sodium sulfate was then filtered off and the resulting material containing a crude product was concentrated at reduced pressure. The crude product was purified by column chromatography resulting in 100.87 g (70.63%) yield of the desired material, dimethyl 5-(1,1,2-trifluoro-2-(perfluoropropoxy)ethoxy)isophthalate.

Example 15

(Dimethyl 5-(1,1,2-trifluoro-2-(1,1,2,3,3,3-hexafluoro-2-(perfluoropropoxy)propoxy)ethoxy)isophthalate

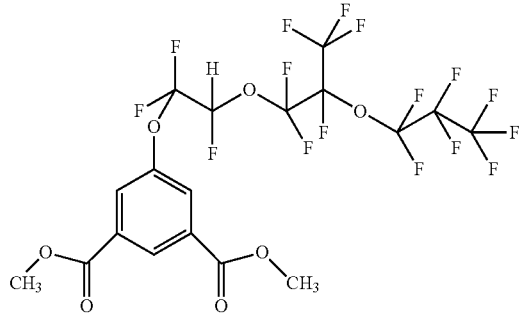 [SMILES: COC(=O)c1cc(OC(F)(F)C(F)OC(F)(F)C(F)(OC(F)(F)C(F)(F)C(F)(F)F)C(F)(F)F)cc(C(=O)OC)c1]

In a dry box, tetrahydrofuran (THF, 1000 mL) and dimethyl 5-hydroxyisophthalate (42.00 g, 0.20 mol) were added to an oven dry round bottom reaction flask equipped with a stirrer to form a reaction mixture. Potassium t-butoxide (6.16 g, 0.055 mol) was added to the reaction flask. 1,1,1,2,2,3,3-Heptafluoro-3-(1,1,1,2,3,3-hexafluoro-3-(1,2,2trifluorovinyloxy)propan-2-yloxy)propane (216 g, 0.50 mol) was then added via the addition funnel to the reaction mixture, and the reaction allowed to stir at room temperature. After 24 hour the reaction was terminated via the addition of 80 mL of 10% HCl. The reaction mixture was concentrated at reduced pressure, diluted with dichloromethane, washed with 10% HCl (2×100 mL) and then with water (2×100 mL), to form an aqueous phase and an organic phase. The separated organic phase was dried over anhydrous sodium sulfate and was then concentrated at reduced pressure to form a crude product. The crude product was purified by column chromatography to give 86.07 g (67.32%) yield of the desired material, dimethyl 5-(1,1,2-trifluoro-2-(1,1,2,3,3,3-hexafluoro-2-(perfluoropropoxy)propoxy)ethoxy)isophthalate.

Examples 16-35

Preparation of: (Dimethyl 2-(1,1,2-trifluoro-2-(1,1,2,3,3,3-hexafluoro-2-(perfluoropropoxy)propoxy)ethoxy)terephthalate (DOE Experiments)

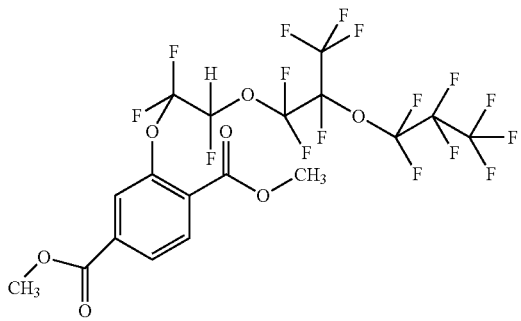 [SMILES: COC(=O)c1ccc(C(=O)OC)c(OC(F)(F)C(F)OC(F)(F)C(F)(OC(F)(F)C(F)(F)C(F)(F)F)C(F)(F)F)c1]

Experimental

In a dry box, tetrahydrofuran (THF, 50 mL) and 1,4-dimethyl-2-hydroxy terephthalate (1.05 g, 0.005 mol) were added to an oven dry round bottom reaction flask equipped with a stirrer to form a reaction mixture. Potassium t-butoxide was added to the reaction mixture, and then the reaction was allowed to reach the desired temperature as shown in the table below. 1,1,1,2,2,3,3-Heptafluoro-3-(1,1,1,2,3,3-hexafluoro-3-(1,2,2-trifluorovinyloxy)propan-2-yloxy)propane was then added to the reaction flask via the addition funnel to form a reaction mixture. After 24 hour the reaction was terminated via the addition of 2 mL of 10% HCl. The reaction mixture was concentrated at reduced pressure, diluted with dichloromethane, washed with 10% HCl (2×50 mL) and then with water (1×50 mL) to form an organic phase and an aqueous phase. The separated organic phase was dried over anhydrous sodium sulfate, then concentrated at reduced pressure and then dried under vacuum. Chloroform (~0.60 g), as an internal standard, was added and the reaction mixture analyzed via proton NMR, showing the production of dimethyl 2-(1,1,2-trifluoro-2-(1,1,2,3,3,3-hexafluoro-2-(perfluoropropoxy)propoxy)ethoxy)terephthalate.

TABLE 1

| Ex. No. | PtType | Blocks | Fluoro-reactant (Mol) | K(t-BuO) (Mol) | Temp (° C.) | % Yield of Fluorinated Product |
|---|---|---|---|---|---|---|
| 16 | −1 | 1 | 0.0125 | 0.0025 | 30 | 47.73 |
| 17 | 1 | 1 | 0.005 | 0.0025 | 60 | 58.76 |
| 18 | −1 | 1 | 0.0125 | 0.001375 | 60 | 70.73 |
| 19 | 1 | 1 | 0.02 | 0.00025 | 60 | 91.63 |
| 20 | −1 | 1 | 0.0125 | 0.001375 | 0 | 25.4 |
| 21 | 1 | 1 | 0.02 | 0.0025 | 60 | 61.66 |
| 22 | 0 | 1 | 0.0125 | 0.001375 | 30 | 88.52 |
| 23 | −1 | 1 | 0.02 | 0.001375 | 30 | 88.6 |
| 24 | 1 | 1 | 0.005 | 0.00025 | 0 | 27.53 |
| 25 | 0 | 1 | 0.0125 | 0.001375 | 30 | 73.62 |
| 26 | 1 | 1 | 0.005 | 0.00025 | 60 | 73.7 |
| 27 | 1 | 1 | 0.005 | 0.0025 | 0 | 32.55 |
| 28 | 0 | 1 | 0.0125 | 0.001375 | 30 | 82.78 |
| 29 | 0 | 1 | 0.0125 | 0.001375 | 30 | 71.7 |
| 30 | −1 | 1 | 0.005 | 0.001375 | 30 | 86.51 |
| 31 | 1 | 1 | 0.02 | 0.0025 | 0 | 21.49 |
| 32 | 0 | 1 | 0.0125 | 0.001375 | 30 | 84.53 |
| 33 | −1 | 1 | 0.0125 | 0.00025 | 30 | 74.59 |
| 34 | 0 | 1 | 0.0125 | 0.001375 | 30 | 80.5 |
| 35 | 1 | 1 | 0.02 | 0.00025 | 0 | 0 |

Example 36

Preparation of 2-(1,1,2-trifluoro-2-(1,1,2,3,3,3-hexafluoro-2-(perfluoropropoxy)propoxy)ethoxy) terephthalic acid

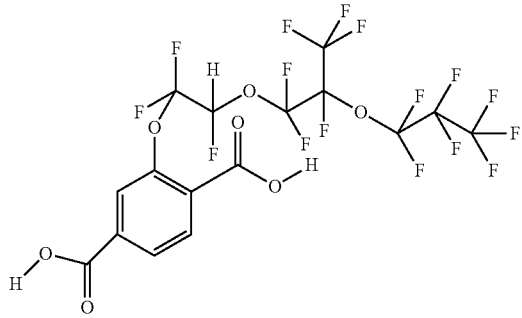 [SMILES: O=C(O)c1ccc(C(=O)O)c(OC(F)(F)C(F)OC(F)(F)C(F)(OC(F)(F)C(F)(F)C(F)(F)F)C(F)(F)F)c1]

Dimethyl 2-(1,1,2-trifluoro-2-(1,1,2,3,3,3-hexafluoro-2-(perfluoropropoxy)-propoxy)ethoxy)terephthalate as prepared in Example 11 (2.25 g, 0.035 mol) was added to a solution of water (50 mL) and potassium hydroxide (KOH, 1.96 g) in a reaction flask. The resulting solution in the reaction flask was heated for 5 hours, cooled to room temperature (about 25° C.) and then acidified by adding concentrated HCl to the reaction flask until a pH of ~1 was achieved, determined by the formation of a precipitate in the reaction flask. The resulting precipitate was filtered and dried under vacuum. Proton NMR of this precipitate showed the desired material, 2-(1,1,2-trifluoro-2-(1,1,2,3,3,3-hexafluoro-2-(perfluoropropoxy)propoxy)ethoxy)terephthalic acid. The precipitate was then crystallized from ethyl acetate (EtOAc, ~1 part) and hexane (~4 parts). After filtration and drying under vacuum, the resulting white di-acid, 2-(1,1,2-trifluoro-2-(1,1,2,3,3,3-hexafluoro-2-(perfluoropropoxy)propoxy)ethoxy)terephthalic acid, had a melting point of 236-239° C.

Example 37

Preparation of 2-(2-chloro-1,1,2-trifluoro-2-(1,1,2,3,3,3-hexafluoro-2-(perfluoropropoxy)propoxy) ethoxy)terephthalic acid

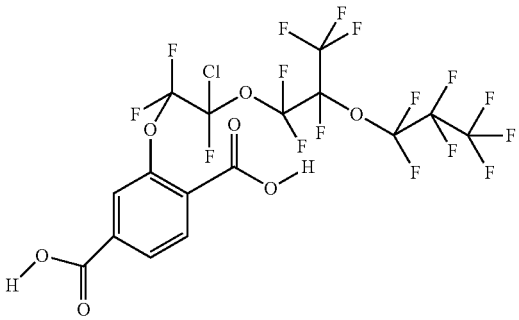

Dimethyl 2-(2-chloro-1,1,2-trifluoro-2-(1,1,2,3,3,3-hexafluoro-2-(perfluoropropoxy)propoxy)ethoxy)terephthalate as prepared in Example 3 (10.00 g, 0.0148 mol) was added to a solution of water (100 mL) and potassium hydroxide (KOH, 8.0 g) in a reaction flask. The resulting solution in the reaction flask was heated to reflux overnight, cooled to room temperature (about 25° C.) and then acidified by adding concentrated HCl to the reaction flask to achieve a pH of ~1, determined by the formation of a precipitate in the reaction flask. The resulting precipitate was filtered and dried under vacuum. NMRs of this precipitate showed the desired material, 2-(2-chloro-1,1,2-trifluoro-2-(1,1,2,3,3,3-hexafluoro-2-(perfluoropropoxy)propoxy)ethoxy)terephthalic acid.

Example 38

Preparation of 2-(2-bromo-1,1,2-trifluoro-2-(1,1,2,3,3-hexafluoro-2-(perfluoropropoxy)propoxy) ethoxy)terephthalic acid

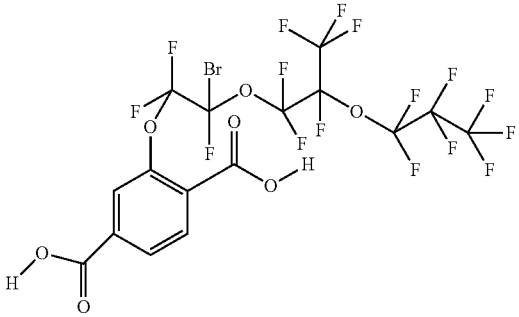 [SMILES: O=C(O)c1ccc(C(=O)O)c(OC(F)(F)C(F)(Br)OC(F)(F)C(F)(OC(F)(F)C(F)(F)C(F)(F)F)C(F)(F)F)c1]

Dimethyl 2-(2-bromo-1,1,2-trifluoro-2-(1,1,2,3,3,3-hexafluoro-2-(perfluoropropoxy)propoxy)ethoxy)terephthalate was prepared using the materials and procedures of Example 3, except that the CCl$_4$ of Example 3 was replaced by CBr$_4$.

10.9 g (0.15 mol) of the thus prepared dimethyl 2-(2-bromo-1,1,2-trifluoro-2-(1,1,2,3,3,3-hexafluoro-2-(perfluoropropoxy)propoxy)ethoxy)terephthalate was added to a solution of water (100 mL) and potassium hydroxide (KOH, 8.0 g) in a reaction flask. The resulting solution in the reaction flask was heated to reflux overnight, cooled to room temperature (about 25° C.) and then acidified by addition of concentrated HCl to the reaction flask until a pH of ~1 was achieved, as determined by the formation of a precipitate. The resulting precipitate was filtered and dried under vacuum, yielding 10.90 g. NMRs (proton and carbon) of this material showed the desired material, 2-(2-bromo-1,1,2-trifluoro-2-(1,1,2,3,3,3-hexafluoro-2-(perfluoropropoxy)propoxy)ethoxy)terephthalic acid.

Example 39

Preparation of 2-(2-chloro-1,1,2-trifluoro-2-(perfluoropropoxy)ethoxy)terephthalic acid

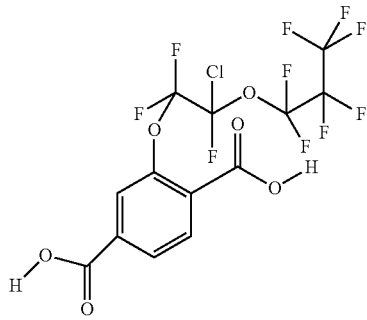 [SMILES: O=C(O)c1ccc(C(=O)O)c(OC(F)(F)C(F)(Cl)OC(F)(F)C(F)(F)C(F)(F)F)c1]

Dimethyl 2-(2-chloro-1,1,2-trifluoro-2-(perfluoropropoxy)ethoxy)terephthalate as prepared in Example 6 (50.00 g, 0.35 mol) was added to a solution of water (726 mL) and potassium hydroxide (KOH, 56.95 g) in a reaction flask. The resulting solution in the reaction flask was heated to reflux overnight, cooled to room temperature (about 25° C.) and then acidified to a pH of ~1 by adding concentrated HCl until a precipitate formed. The resulting precipitate was filtered and dried under vacuum. Proton NMR of this material showed the desired material, 2-(2-chloro-1,1,2-trifluoro-2-(perfluoropropoxy)ethoxy)terephthalic acid.

Example 40

Preparation of 2-(1,1,2-trifluoro-2-(1,1,2,3,3,3-hexafluoro-2-(perfluoropropoxy)propoxy)ethoxy)terephthaloyl dichloride

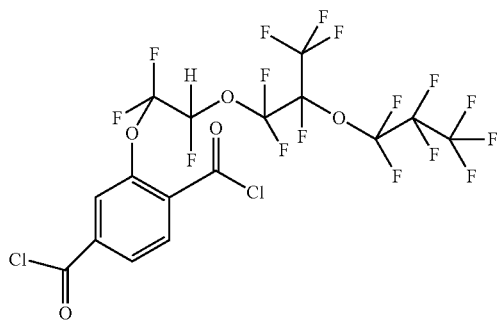 [SMILES: O=C(Cl)c1ccc(C(=O)Cl)c(OC(F)(F)C(F)OC(F)(F)C(F)(OC(F)(F)C(F)(F)C(F)(F)F)C(F)(F)F)c1]

2-(1,1,2-Trifluoro-2-(1,1,2,3,3,3-hexafluoro-2-(perfluoropropoxy)-propoxy)ethoxy)terephthalic acid as prepared in Example 40 (1.129 g) was placed in a round bottom reaction flask equipped with reflux condenser, stirrer and kept under nitrogen. Thionyl chloride (5.8 mL) was added to the reaction flask and the reaction solution heated reflux overnight. The resulting reaction solution was cooled to room temperature (about 25° C.) and the excess thionyl chloride was removed by vacuum, affording the desired compound as determined by NMR, 2-(1,1,2-trifluoro-2-(1,1,2,3,3,3-hexafluoro-2-(perfluoropropoxy)propoxy)ethoxy)terephthaloyl dichloride, as an oil.

Example 41

Preparation of 2-(2-chloro-1,1,2-trifluoro-2-(perfluoropropoxy)ethoxy)terephthaloyl dichloride

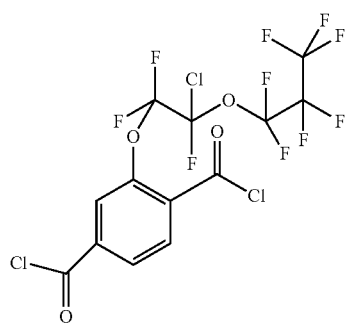 [SMILES: O=C(Cl)c1ccc(C(=O)Cl)c(OC(F)(F)C(F)(Cl)OC(F)(F)C(F)(F)C(F)(F)F)c1]

2-(2-chloro-1,1,2-trifluoro-2-(perfluoropropoxy) ethoxy)terephthalic acid as prepared in Example 43 (50.99 g, 0.1056 mol) was place in an oven-dried round bottom reaction flask equipped with a stirrer, reflux condenser and kept under nitrogen to form a reaction mixture. Thionyl chloride (423 mL) was added to the reaction flask and the resulting reaction mixture was heated to reflux over night. The reaction mixture was cooled to room temperature and the excess thionyl chloride was removed under vacuum. The resulting material was then removed by vacuum distillation to give the desired material as determined by NMR, 2-(2-chloro-1,1,2-trifluoro-2-(perfluoropropoxy)ethoxy)terephthaloyl dichloride, 46.04 g, 74.5% yield, with a boiling point 124-126° C. at 1.1 torr.

Example 42

Preparation of 5-(1,1,2-trifluoro-2-(1,1,2,3,3,3-hexafluoro-2-(perfluoropropoxy)propoxy)ethoxy) isophthaloyl dichloride

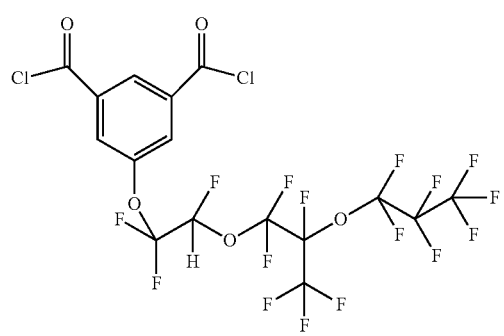 [SMILES: O=C(Cl)c1cc(OC(F)(F)C(F)OC(F)(F)C(F)(OC(F)(F)C(F)(F)C(F)(F)F)C(F)(F)F)cc(C(=O)Cl)c1]

In a dry box, tetrahydrofuran (THF, 1000 mL) and dimethyl 5-hydroxyisophthalate (42.00 g, 0.20 mol) were added to an oven dry round bottom reaction flask equipped with a stirrer to form a reaction mixture. Potassium t-butoxide (6.16 g, 0.055 mol) was added to the reaction flask. 1,1,1,2,2,3,3-Heptafluoro-3-(1,1,1,2,3,3-hexafluoro-3-(1,2,2trifluorovinyloxy)propan-2-yloxy)propane (216 g, 0.50 mol) was then added via the addition funnel to the reaction mixture, and the reaction allowed to stir at room temperature. After 24 hour the reaction was terminated via the addition of 80 mL of 10% HCl. The reaction mixture was concentrated at reduced pressure, diluted with dichloromethane, washed with 10% HCl (2×100 mL) and then with water (2×100 mL), to form an aqueous phase and an organic phase. The separated organic phase was dried over anhydrous sodium sulfate and was then concentrated at reduced pressure to form a crude product. The crude product was purified by column chromatography to give 86.07 g (67.32%) yield of the desired material, dimethyl 5-(1,1,2-trifluoro-2-(1,1,2,3,3,3-hexafluoro-2-(perfluoropropoxy)propoxy)ethoxy)isophthalate.

The thus prepared isophthalate was then hydrolyzed to the corresponding isophthallic acid following the procedures described in Example 36 for the conversion of terephthalate to terephthallic acid, thereby preparing dimethyl 5-(1,1,2-trifluoro-2-(1,1,2,3,3,3-hexafluoro-2-(perfluoropropoxy)propoxy)ethoxy)isophthallic acid.

46.63 g (0.076 mol) of 5-(1,1,2-Trifluoro-2-(1,1,2,3,3,3-hexafluoro-2-(perfluoropropoxy)propoxy)ethoxy)isophthalic acid thus prepared was placed in an oven-dried round bottom reaction flask equipped with a stirrer, reflux condenser and kept under nitrogen to form a reaction mixture. Thionyl chloride (304 mL) was added to the reaction flask and the reaction was heated to reflux over night. The reaction mixture was cooled to room temperature (about 25° C.) and the excess thionyl chloride was removed from the reaction mixture under vacuum, forming a reaction product. The resulting product was then vacuum distilled to give the desired material, 5-(1,1,2-trifluoro-2-(1,1,2,3,3,3-hexafluoro-2-(perfluoropropoxy)propoxy)ethoxy)isophthaloyl dichloride, 38.96 g, 78.8% yield, with a boiling point of 116-123° C. at 0.60 torr.

Example 43

Preparation of 2-(2-bromo-1,1,2-trifluoro-2-(1,1,2,3,3-hexafluoro-2-(perfluoropropoxy)propoxy)ethoxy)terephthaloyl dichloride ((A) ~87%) and 2-(1,1,2-trifluoro-2-(1,1,2,3,3,3-hexafluoro-2-(perfluoropropoxy)propoxy)ethoxy)terephthaloyl dichloride ((B) ~13%)

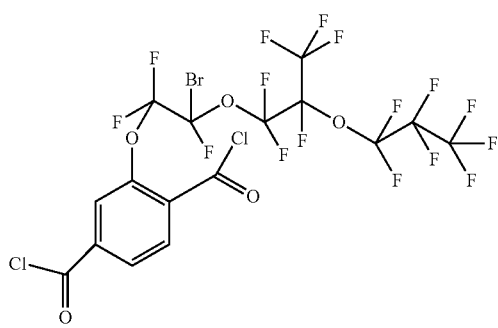

-continued

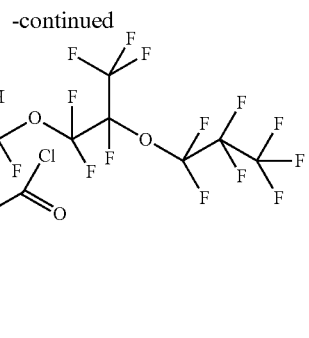

A mixture was prepared containing 87% of the 2-(2-bromo-1,1,2-trifluoro-2-(1,1,2,3,3,3-hexafluoro-2-(perfluoropropoxy)propoxy)ethoxy)terephthalic acid as prepared in Example 38 and 13% of the 2-(1,1,2-trifluoro-2-(1,1,2,3,3,3-hexafluoro-2-(perfluoropropoxy)propoxy)ethoxy)terephthalic acid as prepared in Example 36. 57.70 g of the mixture so formed was placed in an oven-dried round bottom reaction flask equipped with a stirrer, reflux condenser and kept under nitrogen to form a reaction mixture. Thionyl chloride (334 mL) was added to the reaction flask and the reaction mixture was heated to reflux over night. The reaction mixture was cooled to room temperature (about 25° C.) and the excess thionyl chloride was removed from the reaction mixture under vacuum to form a reaction product. The resulting product was then vacuum distilled to give the desired product, 38.96 g, 78.8% yield, with a boiling point of 150-165° C. at ~0.30 torr. Proton NMR showed the product to be a mixture of 2-(2-bromo-1,1,2-trifluoro-2-(1,1,2,3,3,3-hexafluoro-2-(perfluoropropoxy)propoxy)ethoxy)terephthaloyl dichloride (~87%) and 2-(1,1,2-trifluoro-2-(1,1,2,3,3,3-hexafluoro-2-(perfluoropropoxy)propoxy)ethoxy)terephthaloyl dichloride.

Example 44

Preparation of 2-(1,1,2-trifluoro-2-(1,1,2,3,3,3-hexafluoro-2-(perfluoropropoxy)propoxy)ethoxy)terephthalohydrazide

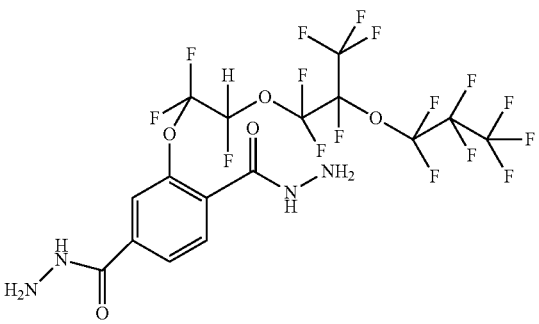 [SMILES: NNC(=O)c1ccc(C(=O)NN)c(OC(F)(F)C(F)OC(F)(F)C(F)(OC(F)(F)C(F)(F)C(F)(F)F)C(F)(F)F)c1]

Dimethyl 2-(1,1,2-trifluoro-2-(1,1,2,3,3,3-hexafluoro-2-(perfluoropropoxy)-propoxy)ethoxy)terephthalate prepared as in Example 10 (4.5 g, 007 mol) and hydrazine monohydrate (2.45 g, 0.49 mol) were placed in a round bottom reaction flask containing methanol (50 mL) to form a reaction mixture. The reaction flask was equipped with a stirrer, reflux condenser and under a nitrogen atmosphere. The reaction mixture was heated to a reflux over night. The reaction mixture was then cooled to room temperature and then poured into water (~500 mL), from which a precipitate resulted. The precipitated solid was filtered and dried under vacuum and then crystallized from ethyl acetate, affording 2.51 of the desired material. NMRs (carbon and proton) analyses showed it to be the desired material, 2-(1,1,2-trifluoro-2-(1,1,2,3,3,3-hexafluoro-2-(perfluoropropoxy)propoxy)ethoxy)terephthalohydrazide.

What is claimed is:

1. A composition comprising a fluorovinyl ether aromatic compound represented by the structure (I)

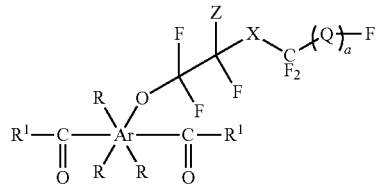

I wherein,
Ar represents a benzene or naphthalene radical;
each R is independently H, $C_1$-$C_{10}$ alkyl, $C_5$-$C_{15}$ aryl, $C_6$-$C_{20}$ arylalkyl; OH, or a radical represented by the structure (II)

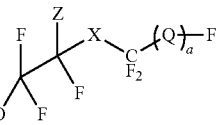

II with the proviso that only one R can be OH or the radical represented by the structure (II);
each $R^1$ is independently OH, $C_1$-$C_{10}$ alkoxy, $C_5$-$C_{15}$ aryloxy, $C_6$-$C_{20}$ arylalkoxy;
chloro, bromo; or amino;
X is O or $CF_2$;
Z is H, Cl, or Br;
Q represents the structure (Ia)

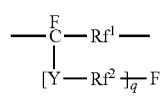

Ia wherein a=0 or 1;
q=0-10;
Y is O or $CF_2$;
$Rf^1$ is $(CF_2)_n$, wherein n is 0-10; and
$Rf^2$ is $(CF_2)_p$, wherein p is 0-10, with the proviso that when p is 0, Y is $CF_2$.

2. The composition of claim 1 wherein Ar is a benzene radical.

3. The composition of claim 1 wherein each R is —H.

4. The composition of claim 1 wherein one R is a radical represented by the structure (II).

5. The composition of claim 1 wherein at least one R is $C_1$-$C_{10}$ alkyl, $C_5$-$C_{15}$ aryl, $C_6$-$C_{20}$ arylalkyl.

6. The composition of claim 1 wherein $R^1$ is —OH.

7. The composition of claim 1 wherein $R^1$ is $C_1$-$C_{10}$ alkoxy, $C_5$-$C_{15}$ aryloxy, $C_6$-$C_{20}$ arylalkoxy.

8. The composition of claim 1 wherein $R^1$ is —Cl or —Br.

9. The composition of claim 1 wherein $R^1$ is chloro.

10. The composition of claim 1 wherein $R^1$ is amino.

11. The composition of claim 1 wherein $R^1$ is

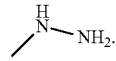

12. The composition of claim 1 wherein Z is —Cl or —Br.

13. The composition of claim 2 wherein each a=1, R is H, $R^1$ is —$OCH_3$, Z is —Cl, X is —O—, Y is —$CF_2$—, n=1, p=0, and q=1.

14. The composition of claim 1 wherein a=0.

15. The composition of claim 1 wherein a=1, q=0, and n=0.

16. A process comprising combining a hydroxy aromatic diester in the presence of a solvent and a catalyst with a perfluorovinyl compound represented by the structure (III)

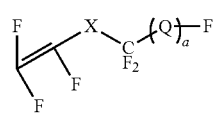

III wherein X is O or $CF_2$, and Q represents the structure (Ia)

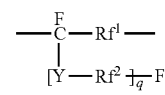

Ia wherein a=0 or 1;
q=0-10;
Y is O or $CF_2$;
$Rf^1$ is $(CF_2)_n$, wherein n is 0-10;
$Rf^2$ is $(CF_2)_p$, wherein p is 0-10, with the proviso that when p is 0, Y is $CF_2$ to form a first reaction mixture, stirring the first reaction mixture at a temperature from about −70° C. to the reflux temperature of the reaction mixture, and cooling, thereby forming a fluorovinyl ether aromatic diester according to claim 1.

17. The process of claim 16 wherein the solvent is not halogenated.

18. The process of claim 16 wherein the solvent is halogenated.

19. The process of claim 16 wherein the catalyst is sodium carbonate or potassium carbonate.

20. The process of claim 16 further comprising: combining the so-formed fluorovinyl ether aromatic diester with an aqueous base to form a second reaction mixture, heating the second reaction mixture to reflux, cooling the second reaction mixture, and adding acid to the second mixture until a pH from 0 to 2 is achieved, to form a fluorovinyl ether aromatic diacid.

21. The process of claim 20 further comprising combining the fluorovinyl ether aromatic diacid with $SOCl_2$, $PCl_3$, or $PCl_5$ to form a third reaction mixture, and heating the third reaction mixture to reflux followed by cooling, to form a fluorovinyl ether aromatic diacid chloride.

22. The process of claim 16 further comprising combining the fluorovinyl ether aromatic diester with an amine to form a fourth reaction mixture, heating the fourth reaction mixture to reflux cooling the fourth reaction mixture, and adding it to water to form a precipitate, to produce a fluorovinyl ether aromatic diamine.

23. The process of claim 22 wherein the amine is hydrazine.

24. The process of claim 16 wherein the perfluorovinyl compound is 1,1,1,2,2,3,3-heptafluoro-3-(1,1,1,2,3,3-hexafluoro-3-(1,2,2-trifluorovinyloxy)propan-2-yloxy)propane, or heptafluoropropyltrifluorovinylether.

* * * * *